United States Patent [19]
Loiselle et al.

[11] Patent Number: 5,985,666
[45] Date of Patent: Nov. 16, 1999

[54] FORAGES

[75] Inventors: François J. Loiselle, Clive; Scott E. Nichols, Johnston, both of Iowa

[73] Assignee: Pioneer Hi-Bred International, Inc., Des Moines, Iowa

[21] Appl. No.: 08/979,514

[22] Filed: Nov. 26, 1997

Related U.S. Application Data

[63] Continuation-in-part of application No. 08/478,704, Jun. 7, 1995, abandoned, and a continuation-in-part of application No. 08/485,243, Jun. 7, 1995, Pat. No. 5,712,107, and a continuation-in-part of application No. 08/482,711, Jun. 7, 1995, abandoned.

[51] Int. Cl.$^6$ ............... C12N 5/04; C12N 15/29; C12Q 1/48; C07H 1/00
[52] U.S. Cl. ............ 435/419; 435/410; 435/412; 435/15; 435/193; 435/278; 435/240.1; 435/252.3; 435/320.1; 536/23.2; 536/123.12; 536/128
[58] Field of Search ............ 435/410, 419, 435/240.1, 193, 252.3, 320.1, 15.4, 278, 885; 536/23.2, 123.12, 123.13, 128

[56] References Cited

U.S. PATENT DOCUMENTS 5,679,880  10/1997  Curtiss, III et al. ............ 800/205

FOREIGN PATENT DOCUMENTS

| | | |
|---|---|---|
| 94/11520 | 5/1994 | WIPO . |
| WO 95/13389 | 5/1995 | WIPO . |
| WO 96/06173 | 2/1996 | WIPO . |

OTHER PUBLICATIONS

Guan et al. Plant Physiol.1994, 104 : 1449–1453, 1994.
Shiroza et al. J. Bacteriol. 1987, 169(9) : 4263–70, 1997.
Armstrong, C. L. The Maize Handbook, Eds. M. Freeling, V. Walbot, 1994, Springer–Verlag, NY, Inc, Chapter 120, pp. 663–671, 1994.

*Primary Examiner*—Ponnathapura Achutamurthy
*Assistant Examiner*—Tekchand Saidha
*Attorney, Agent, or Firm*—Pioneer Hi-Bred International, Inc.

[57] ABSTRACT

A transgenic plant cell is provided containing a DNA molecule encoding an enzyme selected from the group consisting of fructosyltransferase, glucosyltransferase B, mutants of glucosyltransferase B, glucosyltransferase C, glucosyltransferase D, mutants of glucosyltransferase D and functional fragments of each enzyme. A transgenic plant regenerated from the plant cell is also provided. A method of improving the ensilability and the nutritional value of plants is also provided comprising introducing into the cells of the plant an expression cassette comprising the above DNA molecule operably linked to a promoter functional in the cells of the plant to yield transformed plant cells, and regenerating a transformed plant from the transformed cells. The transformed plants also provide improved digestibility in ruminants.

9 Claims, No Drawings

FORAGES

This application is a continuation-in-part of applications U.S. Ser. No. 08/478,704 now abandoned, U.S. Ser. No. 08/485,243, now U.S. Pat. No. 5,712,107; U.S. Ser. No. 08/482,711, now abandoned, all filed Jun. 7, 1995.

FIELD OF THE INVENTION

The present invention relates to improved forages and methods for producing and ensuing same.

BACKGROUND OF THE INVENTION

The storage carbohydrates found in plants, including sucrose, glucans, starch and fructans, are an important source of feed for animals, particularly grazing ruminants. Often these carbohydrates can be of limited availability in pasture plants.

The nutritional value of forage-based diets for ruminants is limited by the microbial efficiency of the rumen. Rumen microorganisms require protein and carbohydrates to synthesize microbial protein and volatile fatty acids. Either the protein or carbohydrate can limit the microbial efficiency. If a diet has high levels of soluble protein, adequate quantities of readily fermentable carbohydrates should be included in the diet to avoid ammonia loss.

Excessive protein degradation in the rumen of animals may be the most limiting nutritional factor in legume or grass pastures or silage. Such pastures have the potential to produce a forage with high protein levels but this protein is not always utilized efficiently. Such pastures exhibits a high protein-low energy imbalance. Due to this energy imbalance, the ruminant fed with a high proportion of legume or grass forage, such as with grazing pure alfalfa, cannot fully benefit from the high protein content of the forage.

The cost of feeding a highly degradable protein source goes beyond the nitrogen losses and reduced microbial efficiency. There is an energy cost in detoxifying excess ammonia resulting from excessive rumen degradable protein. When comparing a 17% crude protein vs. a 19% diet, this maintenance cost is equal to one (1) pound of milk per cow daily (Shultz T. On-line, Milk Lines (July 1997).

hftp//www.ucce.tulare.ca.us/pub/milk0797.htm#MUN

In mammals the detoxification of ammonia is accomplished by the liver through the urea cycle. Carbamoyl phosphate is the starting point of the urea cycle and carbamoyl phosphate synthase uses energy from ATP to fuse a carbon dioxide molecule with an ammonia molecule and a phosphate to make an active form of ammonia that can be added to an acceptor molecule to make urea. (Makemson J. & Kuhn (Online). Amino acid catabolism and the urea cycle.

http://www.fiu.edu/~biology/bch3033/lectures/webureacyc.htm

This maintenance cost is perceived by some animal nutritionists as being the most important cause of reduced efficiency of highly degradable proteins in the feedstuff.

Legume digestibility declines during maturation of the plant as glucose and sucrose are remobilized in the plant and therefore cannot be stored in aerial parts effectively. However, the production of immobile carbohydrate sources such as glucans or fructans in aerial plant parts offer great potential to improve forage digestibility in legumes and grasses.

Good ensuing conditions for forages depend on the quick attainment and maintenance of an oxygen-free condition. The aerobic degradative processes are inhibited through the elimination of atmospheric oxygen, the formation of organic acids and a pH of 4 to 5. (Muck, 1988). The type of further ensuing activity or changes depends on the composition of the crop and the microorganisms present. Crops that have a naturally high level of carbohydrates ferment rapidly, produce a great deal of lactic acid, a low pH, and a generally high silage quality.

Many forages, such as legumes, however, do not produce good natural fermentation. When the level of carbohydrates is low, the amount of acid that is produced is low. Also, the high protein percentage in legumes tends to act as a buffer, as well as a source of ammonia and amine-type compounds, therefore making the attainment of a low pH even more difficult.

Compositional factors are near critical levels so that unfavorable fermentation (low palatability and high spoilage losses) frequently occur unless special precautions are taken. (Barnes and Gordon, 1972). The most popular additive to help the preservation of the forage involve the use of inoculants and the use of acids. Sugars such as molasses are also added to help the pH reduction process.

Extensive conversion of protein to non-protein nitrogen occurring during silage fermentation results in excessive production of ammonia in the rumen. Because milking cows fed high-protein alfalfa as their principal forage may receive as much as 60% of their total protein from the alfalfa, it is important to minimize protein degradation during harvest and storage. Degradation is greatest in the direct-cut silages but wilted alfalfa silages (haylage) may have as much as 20% ammonia N. (Conrad and Klopfenstein, 1988).

Barnes, R. F. & C. H. Gordon. 1972. *Feeding value and on-farm feeding.* pp. 601–630. In: Alfalfa Science and Technology. C. H. Hanson (ed.) No. 15 in the series Agronomy. ASA, Madison, Wis.

Bethard, G. (On-line) Estimating Rumen Available and Nonstructural Carbohydrates in Dairy Cattle Diets. Available hftp://www.cyber.vt.edu/dl/cows/9718.html.

Conrad H. R. & T. J. Klopfenstein. 1988. Role in livestock feeding-greenchop, silage, hay, and Dehy. pp. 539–551 in: Alfalfa and Alfalfa Improvement; C. H. Hanson (ed.). No 29 in the series Agronomy.

Franck, R. 1995. The Balancing Act. *Dairy Herd Management,* February 1995: 50–52.

Muck, R. E. 1988. Factors Influencing Silage Quality and their Implications for Management. *J. Dairy. Sci.* 71: 2992–3002.

Nocek, J. E., and J. B. Russell. 1988. Protein and energy as an integrated system. Relationship of ruminal protein and carbohydrate availability to microbial synthesis and milk production. *J. Dairy Sci.* 71:2070.

Paterson, J. A.; R. L. Belyea, J. P. Bowman, M. S. Kerley & J. E. Williams. 1994. The impact of forage quality and supplementation regimen on ruminant animal intake and performance. pp. 59–114 in: Fahey, G. C. Jr. (ed.) Forage Quality, Evaluation, and Utilization. ASA, CSSA, SSSA, Madison, Wis.

Stokes, S. R., W. H. Hoover, T. K. Miller & R. Blauweikel. 1991. Ruminal digestion and microbial utilization of diets varying in types of carbohydrate and protein. *J. Dairy Sci.* 74: 871–881.

Vagnoni, D. B. & G. A. Broderick. 1995. Effect of Energy supplementation of alfalfa hay or alfalfa silage on protein supply to lactating cows. U.S. Dairy Forage Research Center. 1995 Research Summaries.

Van Keuren, R. W. and A. G. Matches. 1988. Pasture production and utilization. pp. 515–551 in: Alfalfa and Alfalfa Improvement; C. H. Hanson (ed.). No 29 in the series Agronomy.

SUMMARY OF THE INVENTION

It is an object of the present invention to provide a forage with improved properties for ensiling.

It is another object of the present invention to provide a forage with improved nutritional value for ruminants.

It is another object of the present invention to provide a forage with improved digestibility.

It is another object of the present invention to provide a forage with reduced protein degradation during handling and ensiling.

It is another object of the present invention to provide a method for increasing the nutritional value of forage.

It is another object of the present invention to provide a method for improving the silability of plants.

According to the present invention a transgenic plant cell is provided containing a DNA molecule encoding an enzyme selected from the group consisting of fructosyltransferase, glucosyltransferase B, mutants of glucosyltransferase B, glucosyltransferase C, mutants of glucosyltransferase C, glucosyltransferase D, mutants of glucosyltransferase D and functional fragments of each enzyme. Transgenic plants regenerated from transformed cells are also provided.

Methods of increasing the ensilability and the nutritional value of plants are also provided comprising introducing into the cells of the alfalfa plant an expression cassette comprising the above DNA molecule operably linked to a promoter functional in the cells of the plant to yield transformed plant cells, and regenerating a transformed plant from the transformed cells.

DETAILED DESCRIPTION OF THE INVENTION

As used herein, "glucan" means a glucose polymer produced by the glucosyltransferase enzymes described herein. The glucan has linkages that are primarily $\alpha(1\to3)$, $\alpha(1\to6)$, with branching achieved primarily through $\alpha(1\to3,6)$ linkages and other minor branch points such as $\alpha(1\to2,3,6)$, $\alpha(1\to3,4,6)$ etc.

As used herein, "vacuole" means the cellular compartment bounded by the tonoplast membrane.

As used herein, "amyloplast" means starch accumulating organelle in plant storage tissue.

As used herein "expression cassette" means a complete set of control sequences including promoter, initiation, and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence.

As used herein "functional fragment" of a glucosyltransferase gene or fructosyltransferase gene refers to a nucleic acid molecule that encodes a portion of a glucosyltransferase polypeptide which possesses glucosyltransferase activity or fructosyltransferase activity respectively. A "functional fragment" of a glucosyltransferase enzyme or fructosyltransferase enzyme is a polypeptide exhibiting glucosyltransferase or fructosyltransferase activity respectively.

*Streptococcus mutans* is a species that is endogenous to the oral cavity and colonizes tooth enamel.

Kuramitsu, "Characterization of Extracellular Glucosyl Transferase Activity of *Streptococcus-mutans.*" *Infect. Immun.*; Vol. 12(4); pp. 738–749; (1975); and Yamashita, et al., "Role of the *Streptococcus-Mutans*-gtf Genes in Caries Induction in the Specific-Pathogen-Free Rat Model," *Infect. Immun.*; Vol. 61(9); pp. 3811–3817; (1993); both incorporated herein their entirety by reference.

*Streptococcus mutans* species secrete several glucosyltransferase enzymes which utilize dietary sucrose to make a variety of extracellular soluble and insoluble glucans. In a preferred embodiment, insoluble glucans are produced in a transgenic plant. It is believed that insoluble glucans are less likely to interfere with the normal functioning of the plant.

Both soluble and insoluble glucans and fructans are synthesized. The proteins responsible have been isolated and characterized. See e.g.

Aoki, et al., "Cloning of a *Streptococcus-mutans* Glucosyltransferase Gene Coding for Insoluble Glucan Synthesis," *Infect. Immun.* Vol. 53 (3) pp. 587–594 (1986);

Shimamura, et al., "Identification of Amino Acid Residues in *Streptococcus Mutans* Glucosyltransferases Influencing the Structure of the Glucan Produced," *J. Bacteriol.*, Vol. 176 (16) pp. 4845–50 (1994) and Kametaka, et al., "Purification and Characterization of Glucosyltransferase from *Streptococcus-mutans* OMZ176 with Chromatofocusing," *Microbios,* Vol. 51(206) pp. 29–36; (1987); all incorporated herein their entirety by reference.

Handada et al., "Isolation and Characterization of the *Streptococcus mutans* ftf Gene, Coding for Synthesis of Both Soluble and Insoluble Glucans," *Infect. Immun.,* Vol. 56 (8) pp. 1999–2005 (1988) and Honda, et al., "Nucleotide Sequence of the *Streptococcus mutans* gtfD Gene Encoding the Glucosyltransferase-S Enzyme", *J. Gen. Microbial.,* Vol. 136 pp. 2099–2105 (1990) incorporated herein by reference.

The proteins involved are large (~155 kDa) and catalyze the group transfer of the glucosyl portion of sucrose to an acceptor glucan via $(1\to3)$ and $(1\to6)$ linkages.

Wenham, et al., "Regulation of Glucosyl Transferase and Fructosyl Transferase Synthesis by Continuous Cultures of *Streptococcus-mutans,*" *J. Gen. Microbiol.*; Vol. 114 (Part 1); pp. 117–124; (1979);

Fu, et al., "Maltodextrin Acceptor Reactions of *Streptococcus-mutans* 6715 glucosyltransferases," *Carbohydr. Res.*; Vol. 217; pp. 210–211; (1991); and Bhattacharjee, et al., "Formation of Alpha-$(1\to6)$, Alpha-$(1\to3)$, and Alpha $(1\to2)$Glycosidic Linkages by Dextransucrase from *Streptococcus Sanguis* in Acceptor-Dependent Reactions," *Carbohydr. Res.*; Vol. 242; pp. 191–201; (1993); all incorporated herein their entirety by reference.

The genes encoding enzymes involved in glucan synthesis have been isolated and sequenced.

Russell, et al., "Expression of a Gene for Glucan-binding Protein from *Streptococcus-mutans* in *Escherichia-coli,*" *J. Gen. Microbiol.,* Vol. 131(2) pp. 295–300 (1985);

Russell et al., "Characterization of Glucosyltransferase Expressed from a *Streptococcus-Sobrinus* Gene Cloned in *Escherichia-coli,*" *J. Gen. Microbiol.,* Vol. 133(4) pp. 935–944 (1987) and Shiroza, et al., "Sequence Analysis of the GTF B Gene from *Streptococcus mutans,*" *J. Bacteriol.*; Vol. 169(9); pp. 4263–4270; (1987);

Shimamura, et al., "Identification of Amino Acid Residues in *Streptococcus Mutans* Glucosyltransferases Influencing the Structure of the Glucan Produced," *J. Bacteriol.*, Vol. 176 (16) pp. 4845–50 (1994) all incorporated herein in their entirety by reference.

The structures of the various glucans produced by glucosyltransferase enzymes are quite heterogeneous with respect to the proportions of (1→3), (1→6) and (1→3,6) branches present in any given glucan.

Glucosyltransferase or fructosyltransferase enzyme activity incorporated into the vacuole and/or amyloplast of a plant cell leads to the accumulation of starch, glucan and fructan in the same vacuole and/or amyloplast. Transformation of genes which encode naturally occurring fructosyltransferase, glucosyltransferase, glucosyltransferase mutants, and functional fragments of the enzymes into plants, provides a plant with increased digestibility for ruminants and improved ensilability.

The wild type glucosyltransferase and mutants thereof useful in producing glucans according to the present invention are provided below. The following code is employed:

| Amino Acid | One-letter Symbol |
|---|---|
| Alanine | A |
| Asparagine | N |
| Aspartic Acid | D |
| Glutamine | Q |
| Glutamic Acid | E |
| Isoleucine | I |
| Lysine | K |
| Threonine | T |
| Tyrosine | Y |
| Valine | V |

The nomenclature used to identify the mutant glucosyltransferase enzymes used to produce the present glucans is as follows: the number refers to the amino acid position in the polypeptide chain; the first letter refers to the amino acid in the wild type enzyme; the second letter refers to the amino acid in the mutated enzyme; and enzymes with multiple mutations have each mutation separated by /.

The glucosyltransferase B enzyme used to produce glucans is preferably selected from the group consisting of the wild type, 1448V, D457N, D567T,K1014T, D457N/D567T, D457N/D571K, D567T/D571 K, D567T/D571K/K1014T, 1448V/D457N/D567T/D571K/K779Q/K1014T and Y169A/Y170A/Y171A.

The glucosyltransferase D gene enzyme used to produce glucans is preferably selected from the group consisting of the wild type, T589D, T589E, N471D, N471D/T589D and N471D/T589E.

In a preferred embodiment, insoluble glucans are produced by mutants of glucosyltransferase B, 1448V, D457N, D567T,K1014T, D457N/D567T, D457N/D571K, D567T/D571K, D567T/D571K/K1014T, 1448V/D457N/D567T/D571K/K779Q/K1014T and Y169A/Y170A/Y171A and mutants of glucosyltransferase D, T589D and T589E.

Various genes encoding enzymes involved in fructan synthesis have also been isolated and sequenced. Any such gene known in the art can be utilized in the transformation of the plants.

Sprenger, N., et al., Purification, cloning, and functional expression of sucrose:fructan 6-fructosyltransferase, a key enzyme of fructan synthesis in barley, *Proc. Natl. Acad. Sci.* 92 (25), 11652–11656 (1995).

S. de Halleux and P. Van Cutsem, Cloning and Sequencing of the 1-SST cDNA from Chicory Root, (Accession No. U81520) (PGR97-036), Plant Physiol. 113, 1003 (1997).

Smeekens, J. C., et al. Production of Oligosaccharides in Transgenic Plants, Patent: WO 9601904-A 3 JAN. 25, 1996.

Giffard, P. M., et al., The ftf encoding the cell-bound fructosyltransferase of *Streptococcus salivarius* ATCC 25975 is preceded by an insertion sequence and followed by FUR1 and clpP homologues, *J. Gen. Microbiol.* 139, 913–920 (1993).

Rathsam, C., Giffard, P. M. and Jacques, N. A., The cell-bound fructosyltransferase of *Streptococcus salivarius:* the carboxyl terminus specifies attachment in a *Streptococcus gordonii* model system, J. Bacteriol. 175 (14), 4520–4527 (1993).

Suitable plants include alfalfa (*Medicago sativa* L.), white clover (*Trifolium repens* L.), red clover (*Trifolium pratense* L.), birdsfoot trefoil (*Lotus cornitulatus* L.), lespedeza (*Lespedeza cuneata* L.), sainfoin (*Onobrychis sativa* Lam), corn (*Zea mays* L.), sorghum (*Sorghum bicolor* Moench), tall fescue (*Festuca arundinacea* Schreb.), orchardgrass (*Dactylis glomerata* L.), Italian raygrass (*Lolium multiflorum* Lam.), perennial ryegrass (*Lolium perenne* L.), timothy (*Phleum partense* L.) and other grass species (Bromus spp.; Pennisetum spp.), rye, wheat, barley, oats, millet, triticale, and rice. The glucans and fructans of the present invention are preferably produced in transgenic legumes or grass, and most preferably in legumes such as alfalfa, white clover, red clover, and birdsfoot trefoil.

The production of the present transgenic plants is performed according to methods of transformation that are well known in the art. The glucans and fructans are synthesized by insertion of an expression cassette containing a structural gene which, when transcribed and translated, yields a glucosyltransferase or fructosyltransferase enzyme that produces the desired glucan or fructan.

Such empty expression cassettes, providing appropriate regulatory sequences for plant expression of the desired sequence, are also well-known, and the nucleotide sequence for the gene, either RNA or DNA, can readily be derived from the amino acid sequence for the enzyme using standard texts and the references provided. The above-mentioned genes preferably employ plant-preferred codons to enhance expression of the desired enzyme.

The following description further exemplifies the compositions of this invention and the methods of making and using them. However, it will be understood that other methods, known by those of ordinary skill in the art to be equivalent, can also be employed.

The genes which encode the enzymes or functional fragments can be inserted into an appropriate expression cassette and introduced into cells of a plant species. Thus, an especially preferred embodiment of this method involves inserting into the genome of the plant a DNA sequence encoding a fructosyltransferase gene or a mutant or wild type glucosyltransferase gene in proper reading frame, together with transcription promoter and initiator sequences active in the plant.

The expression cassette comprising the structural gene of this invention operably linked to the desired control sequences can be ligated into a suitable cloning vector. In general, plasmid or viral (bacteriophage) vectors containing replication and control sequences derived from species compatible with the host cell are used.

Transcription and translation of the DNA sequence under control of the regulatory sequences causes expression of the enzyme sequence at levels which provide an elevated amount of the enzyme in the tissues of the plant.

Synthetic DNA sequences can be prepared which encode the appropriate sequence of amino acids of the selected glucosyltransferase or fructosyltransferase enzyme or functional fragments of the enzymes, and this synthetic DNA sequence can be inserted into an appropriate plant expression cassette. Numerous plant expression cassettes and vectors are well known in the art.

As used herein "vector" means a DNA sequence which is able to replicate and express a foreign gene in a host cell. Typically, the vector has one or more restriction endonuclease recognition sites which may be cut in a predictable fashion by use of the appropriate enzyme.

Such vectors are preferably constructed to include additional structural gene sequences imparting antibiotic or herbicide resistance, which then serve as markers to identify and separate transformed cells. As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of a single or a plurality of markers.

Typical selectable markers include genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Genes coding for resistance to herbicides include genes which act to inhibit the action of acetolactate synthase (ALS), in particular the sulfonylurea-type herbicides (e.g., the acetolactate synthase (ALS) genes containing mutations leading to such resistance in particular the S4 and/or Hra mutations), genes coding for resistance to herbicides which act to inhibit action of glutamine synthase, such as phosphinothricin or basta (e.g., the Pat or bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. In Enzymol., 153:253–277 (1987). These vectors are plant integrating vectors in that on transformation, the vectors integrate a portion of vector DNA into the genome of the host plant.

A particularly preferred vector is a plasmid, by which is meant a circular double-stranded DNA molecule which is not a part of the chromosomes of the cell. Exemplary *A. tumefaciens* vectors useful herein are plasmids pKYLX6 and pKYLX7 of Schardi et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A cell in which the foreign genetic material in a vector is functionally expressed has been "transformed" by the vector and is referred to as a "transformant".

Either genomic DNA or cDNA encoding the gene of interest may be used in this invention. The gene of interest may also be constructed partially from a cDNA clone and partially from a genomic clone.

When the gene of interest has been isolated, genetic constructs are made which contain the necessary regulatory sequences to provide for efficient expression of the gene in the host cell.

According to this invention, the genetic construct will contain (a) a genetic sequence coding for the enzyme or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes, including bacterial hosts such as *E. coli, S. typhimurium,* and *Serratia marcescens*. Eukaryotic hosts such as yeast or filamentous fungi may also be used in this invention. Since these hosts are also microorganisms, it will be essential to ensure that plant promoters which do not cause expression of the enzyme in bacteria are used in the vector.

The isolated cloning vector will then be introduced into the plant cell using any convenient technique, including electroporation (in protoplasts), PEG poration, retroviruses, particle bombardment, silicon fiber delivery and microinjection into plant cells, such as protoplasts or embryogenic callus, in cell or tissue culture to provide transformed plant cells containing as foreign DNA at least one copy of the DNA sequence of the plant expression cassette.

The introduction of DNA constructs using polyethylene glycol precipitation is described in Paszkowski et al., *Embo J.* 3: 2717–22 (1984). Electroporation techniques are described in Fromm et al., *Proc. Natl. Acad. Sci.* 82: 5824 (1985). Ballistic transformation techniques are described in Klein et al., *Nature* 327: 70–73 (1987). *Agrobacterium tumefaciens*-mediated transformation techniques are well described in the scientific literature. See for example Horsch et al., *Science* 233: 496–498 (1984) and Fraley et al., *Proc. Natl. Acad. Sci.* 80: 4803 (1983).

Other methods of transfection or transformation include (1) Agrobacterium rhizogenes-mediated transformation (see, e.g. Lichtenstein and Fuller In: Genetic Engineering, vol. 6, PWJ Rigby, ed., London, Academic Press, 1987 and Lichtenstein, C. P. and Draper, J. In: DNA Cloning, Vol. II D. M. Glover, Ed., Oxford, IRI Press, 1985). Application PCT/US87/02512 (WO 88/02405 published Apr. 7, 1988) describes the use of *A rhizogenes* strain A4 and its Ri plasmid along with *A. Tumefaciens* vectors pARC8 or pARC16(2) liposome-mediated DNA uptake (see e.g., Freeman et al., *Plant Cell Physiol.* 25: 1353, 1984), (3) the vortexing method (see e.g. Kindle, *Proc. Natl. Acad. Sci., USA* 87: 128, (1990).

DNA can also be introduced into plants by direct DNA transfer into pollen as described by Zhou et al., *Methods in Enzymology,* 101:433 (1983); D. Hess, *Intern. Rev. Cytol.,* 107:367 (1987); Luo et al., *Plant Mol. Biol. Reporter,* 6: 165 (1988).

Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987) and Benbrook et al., in Proceedings Bio Expo 1986, Butterworth, Stoneham, Mass., pp. 27–54 (1986). A variety of plant viruses that can be employed as vectors are known in the art and include cauliflower mosaic virus (CaMV), geminivirus, brome mosaic virus and tobacco mosaic virus.

Using known techniques, protoplasts can be regenerated and cell or tissue culture can be regenerated to form whole fertile plants which carry and express the gene for an enzyme according to this invention. Accordingly, a highly preferred embodiment of the present invention is a transformed alfalfa plant, the cells of which contain at least one copy of the DNA sequence of an expression cassette of a fructosyltransferase gene or glucosyltransferase gene.

It will also be appreciated by those of ordinary skill that the plant vectors provided herein can be incorporated into *Agrobacterium tumefaciens*, which can then be used to transfer the vector into susceptible plant cells, primarily from dicotyledonous species.

Thus, this invention provides a method for introducing fructosyltransferase genes or glucosyltransferase genes into *Agrobacterium tumefaciens*-susceptible dicotyledonous plants. The expression cassette is introduced into the cells by infecting the cells with *Agrobacterium tumefaciens*, a plasmid of which has been modified to include a plant expression cassette of this invention.

A typical transformation cassette comprises a Brassica ALS3 promoter (WO 96/30530) or a SuperMAS promoter, followed by the relevant glucosyltransferase or fructosyltransferase coding sequence. Typical termination and initiation sequences include Arabidopsis SSU 5' (Krebbers et al., Plant Molec. Bio. 11: 745–59, 1988) and tobacco SSU 3' (Masure and Chiu, Nucleic Acids Res. 13: 2373, 1985).

The transgenic cassette is placed into a transformation vector. For example, BIN19, or derivatives thereof, are useful when transforming via *Agrobacterium tumefaciens*. See e.g. Visser, et al., "Transformation of Homozygous Diploid Potato with an *Agrobacterium-tumefaciens* Binary Vector System by Adventitious Shoot Regeneration on Leaf and Stem Segments," *Plant Mol. Biol.;* Vol. 12(3); pp. 329–338; (1989); incorporated herein in its entirety by reference.

Signal sequences useful in directing the enzyme into the vacuole for accumulation within the vacuole are well known in the art. For vacuolar targeting, see e.g. WO 95/13389 and Ebskamp, et al., "Accumulation of Fructose Polymers in Transgenic Tobacco," *Bio/technology;* Vol. 12; pp. 272–275; (1994); incorporated herein in its entirety by reference. Typical targeting sequences include cysteine protease, barley lectin (U.S. Pat. No. 5,525,713 and Bednarek and Raikel, *Plant Cell* 3: 1195–1206, 1991) and tobacco chitinase (AU-A-78415/91 and Neuhaus et al. Proc. Nat. Acad. Sci 88: 10362–66, 1991).

Preferably the glucans and/or fructans produced by the present enzymes are present in the plants in an amount of from about 0.25 to about 15 weight percent as dry weight, more preferably from about 0.25 to about 12 weight percent, more preferably from about 0.25 to about 8 weight percent.

The transgenic plants are then ready to be fed to animals by means of grazing or silage. Although the present invention provides particular advantage for feeding ruminant animals, the invention also has application for increasing the nutritional value of food and feed products for humans and all varieties of animals, including exotic varieties.

Preparation of silage can be carried out by any method known in the art. In general terms the plants are chopped and placed under oxygen-limiting conditions, such as in a silo. Aerobic respiration begins immediately upon chopping of silage. During this early phase, soluble carbohydrates in the plant tissue are oxidized and converted to carbon dioxide and water. This process will continue until either the oxygen level is depleted or the water soluble carbohydrates are exhausted. Under ideal conditions, with adequate packing and sealing of the ensiled material, respiration lasts only a few hours. Once aerobic conditions are depleted, anaerobic conditions are established, and anaerobic bacteria proliferate.

It is also within the scope of the invention to use inoculants to help preserve silage. For example, inoculation with lactic acid bacteria during the fermentation phase can be beneficial to the fermentation process, see for example U.S. Pat. No. 4,842,871 issued Jun. 27, 1989; U.S. Pat. No. 4,820,531 issued Apr. 11, 1989; U.S. Pat. No. 4,743,454 issued May 10, 1988; and U.S. Pat. No. 4,981,705 issued Jan. 1, 1991. Preferably the inoculant is specifically engineered to utilize fructans and/or glucans as an energy source.

All publications cited in this application are indicative of the level of skill of those skilled in the art to which this invention pertains. All publications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What claimed is:

1. A transgenic plant cell containing a DNA from *Streptococcus mutans* and encoding the glucosyltransferase B enzyme or an enzymatically active fragment thereof.

2. The plant cell of claim 1 wherein the enzyme is targeted to a vacuole or amyloplast of the cell.

3. The plant cell of claim 1 wherein the plant cell is derived from a plant selected from the group consisting of alfalfa, white clover, red clover, birdsfoot trefoil, lespedeza, sainfoin, sorghum, tall fescue, orchard grass, Italian raygrass, perennial ryegrass, timothy, brome grass, corn, rye, barley, wheat, sorghum, oats, millet, triticale, and rice.

4. The plant cell of claim 3 which is derived from a legume or grass.

5. A transgenic plant regenerated from the plant cell of claim 1.

6. The plant cell of claim 1, wherein the plant cell is a forage plant cell.

7. The plant of claim 5, wherein the plant is a forage plant.

8. The plant of claim 7, wherein the plant is an alfalfa, white clover, red clover, birdsfoot trefoil, lespedeza, sainfoin, tall fescue, orchard grass, Italian raygrass, perennial ryegrass, timothy, brome grass, corn, rye, barley, wheat, sorghum, oats, millet, triticale or rice.

9. The plant of claim 8, wherein the plant is an alfalfa, white clover, red clover, birdsfoot trefoil, lespedeza, sainfoin, sorghum, tall fescue, orchard grass, Italian raygrass, perennial ryegrass, timothy, brome grass, triticale or rice.

* * * * *

UNITED STATES PATENT AND TRADEMARK OFFICE
CERTIFICATE OF CORRECTION

PATENT NO. : 5,985,666
DATED : November 16, 1999
INVENTOR(S) : Francois J. Loiselle, Scott E. Nichols It is certified that error appears in the above-identified patent and that said Letters Patent is hereby corrected as shown below:

<u>Title page,</u>
Item [75] Inventors: please insert the following:

[75] Inventors: Francois J. Loiselle, Clive; Scott E. Nichols, Johnston, both of Iowa
Colin Leslie Dow Jenkins, Evatt; Richard J. Simpson, Murrumbateman, both of Australia Item [73] Assignee: Pioneer Hi-Bred International, Inc., Des Moines, Iowa
CSIRO Plant Industry, Canberra, ACT Australia Signed and Sealed this Nineteenth Day of March, 2002

Attest:

JAMES E. ROGAN
*Director of the United States Patent and Trademark Office*

*Attesting Officer*